(12) United States Patent
Lian et al.

(10) Patent No.: US 8,060,198 B2
(45) Date of Patent: Nov. 15, 2011

(54) METHOD AND APPARATUS FOR GENERATING A COMPOSITE FARFIELD ELECTROGRAM

(75) Inventors: Jie Lian, Beaverton, OR (US); Garth Garner, Tigard, OR (US); Hannes Kraetschmer, West Linn, OR (US); Dirk Müssig, West Linn, DE (US)

(73) Assignee: Biotronik CRM Patent AG, Baar (CH)

( * ) Notice: Subject to any disclaimer, the term of this patent is extended or adjusted under 35 U.S.C. 154(b) by 1110 days.

(21) Appl. No.: 11/848,824

(22) Filed: Aug. 31, 2007

(65) Prior Publication Data
US 2008/0065161 A1   Mar. 13, 2008

Related U.S. Application Data

(60) Provisional application No. 60/842,920, filed on Sep. 7, 2006.

(51) Int. Cl.
*A61N 1/362* (2006.01)
*A61B 5/0456* (2006.01)

(52) U.S. Cl. .......................................... 607/5; 600/510

(58) Field of Classification Search .................. 607/4, 5, 607/32; 600/509, 510
See application file for complete search history.

(56) References Cited

U.S. PATENT DOCUMENTS

| | | | |
|---|---|---|---|
| 5,184,615 A | 2/1993 | Nappholz et al. |
| 5,265,602 A | 11/1993 | Anderson et al. |
| 5,331,966 A | 7/1994 | Bennett et al. |
| 5,740,811 A | 4/1998 | Hedberg et al. |
| 6,505,067 B1 | 1/2003 | Lee et al. |
| 6,512,940 B1 | 1/2003 | Brabec et al. |
| 6,522,915 B1 | 2/2003 | Eballos et al. |
| 6,564,106 B2 | 5/2003 | Guck et al. |
| 6,631,290 B1 | 10/2003 | Guck et al. |
| 6,658,283 B1 | 12/2003 | Bornzin et al. |
| 6,813,514 B1 | 11/2004 | Kroll et al. |

OTHER PUBLICATIONS

European Search Report, dated Feb. 20, 2008.

*Primary Examiner* — Carl H. Layno
*Assistant Examiner* — Tammie K Heller
(74) *Attorney, Agent, or Firm* — ARC IP Law, PC; Joseph J. Mayo

(57) ABSTRACT

Method and apparatus that uses dual-chamber (RA-RV), three-chamber (BiA-RV, or RA-BiV), or four-chamber (BiA-BiV) implantable cardiac devices including pacemakers, defibrillators and cardioverters, which stimulate cardiac tissue electrically to control the patient's heart rhythm. The method and apparatus are further configured to create a far-field intra-atrial electrogram (AEGM) and a far-field intra-ventricular electrogram (VEGM) that are independently filtered, scaled, and then summed to form a composite far-field electrogram.

24 Claims, 12 Drawing Sheets

AEGM

VEGM

SECG

Lead-free ECG

METHOD AND APPARATUS FOR GENERATING A COMPOSITE FARFIELD ELECTROGRAM

This application claims benefit of U.S. Provisional Patent Application Ser. No. 60/842,920, filed 7 Sep. 2006, the specification of which is hereby incorporated herein by reference

BACKGROUND OF THE INVENTION

1. Field of the Invention

Embodiments of the invention described herein pertain to the field of medical devices. More particularly, but not by way of limitation, one or more embodiments of the invention enable a method and apparatus for generating a composite far-field electrogram.

2. Description of the Related Art

During pacemaker or ICD follow-up, the surface ECG (SECG) is routinely measured to examine the status of the electrical conduction system of the heart, and to confirm the normal functionality of the implant device, for instance, to verify pacing capture control and ensure proper arrhythmia detection. However, measuring SECG is associated with several drawbacks. First, it increases the duration of the follow-up time and adds to the overall cost. Second, skin preparation and electrode handling may bring considerable inconvenience to the patient, particularly for the females. Third, from one follow-up session to another, the electrodes may not be placed at the exact same locations on the patient, thus resulting in somewhat different SECG. Fourth, externally attached electrodes are subject to motion artifacts from postural changes and the relative displacement between the skin and the electrodes. Finally, the SECG is known to be susceptible to interference such as muscle noise, power line interference, baseline drift from respiration or motion, etc.

Therefore, there is a need to provide the implant device Lead-Free ECG feature, that is, to provide a means to generate the SECG-like signal without the need for attaching the skin electrodes to the patients.

One method for Lead-Free ECG is based on subcutaneous electrodes or subcutaneous electrode array (SEA). For example, U.S. Pat. No. 5,331,966 issued to Bennett et al. discloses a method and apparatus for providing SECG-like signals via an array of relatively closely spaced subcutaneous electrodes located on the body of an implanted device. In a typical embodiment, an array of three electrodes disposed orthogonally on the surface of the pulse generator and connector block and facing outwardly towards the patient's skin is employed to develop the far-field IEGM signal comprising the PQRST signals that are similar to the SECG.

Several patents were issued to further improve the design of the SEA. For example, U.S. Pat. No. 6,522,915 discloses an alternate method and apparatus for detecting electrical cardiac signals via a SEA located on a shroud circumferentially placed on the perimeter of an implanted pacemaker. U.S. Pat. No. 6,512,940 by Brabec et al. disclosed the use of a spiral electrode using in conjunction with the shroud described in the Ceballos et al. disclosure. In addition, U.S. Pats. Nos. 6,564,106 and 6,631,290, both issued to Guck and Donders, disclosed the use of sensing electrodes placed into recesses incorporated along and into the peripheral edge of the implantable pacemaker.

Furthermore, U.S. Pat. No. 6,505,067 issued to Lee et al. discloses a system and method for deriving a virtual SECG based on the signals recorded by the SEA. The SEA consists of at least three (preferably 3 or 4) subcutaneous electrodes located on the surface of the implant device. The signals recorded between these electrodes form independent directional vectors. The method used to determine the virtual SECG is based on vector arithmetic principles.

Although the far-field IEGM recorded by the SEA may approximate the SECG, the disadvantage is the need for special design, fabrication, and manufacture of the SEA and the associated circuits, which add to the hardware complexity.

A different approach for Lead-Free ECG is based on far-field IEGM recorded by existing implant device and the lead system. For example, U.S. Pat. No. 5,265,602 issued to Anderson et al. disclosed a pacemaker, which has a special sense configuration that records the IEGM between the RA ring and the RV ring electrodes. The 'RA ring-RV ring' far-field IEGM is relatively unaffected by the after-potentials and polarization effects, but its morphology is generally quite different from SECG.

Similar approach is disclosed in U.S. Pat. No. 6,658,283 issued to Bornzin et al. According to this disclosure, far-field IEGM is recorded from various lead configurations between wide spaced electrodes including RA tip, RV tip, RA ring, RV ring, and case (including the 'RA ring-RV ring' configuration). The recorded far-field IEGM is further processed by a cascade of linear filters with designed output frequency band to generate the Lead-Free ECG, which according to our experience, is not satisfactory in terms of signal amplitude and morphology.

Another approach is disclosed in U.S. Pat. No. 5,740,811 issued to Hedberg et al. This invention also disclosed multiple lead configurations for measuring the far-field IEGM. One or more channels of the far-field IEGM are first pre-processed (amplified, filtered, blocked, transferred), then post-processed by a pre-trained artificial neural network or fuzzy logic to generate the Lead-Free ECG. However, the artificial neural network or fuzzy logic trained from one dataset may not be applicable to another dataset.

U.S. Pat. No. 6,813,514 issued to Kroll et al. discloses a method to emulate the multi-lead SECG by solving the forward problem. Each channel of SECG or IEGM is converted into a time-varying vector. The SECG matrix (containing multiple SECG vectors) is linearly linked to the IEGM matrix (containing multiple IEGM vectors) by a transfer matrix, which can be pre-calculated by solving the inverse problem. However, this method requires multi-channel IEGM recordings. Moreover, calibration of different transfer matrices is needed to account for different factors affecting the relative locations of the internal leads, such as respiration and posture.

BRIEF SUMMARY OF THE INVENTION

It is an object of the invention to provide a device and/or a system and/or a method providing improved acquisition of an electrogram similar to the SECG.

In view of the forgoing descriptions, the present invention provides an advanced Lead-free ECG method and apparatus. In this disclosure, the following terms are used:

| Term | Description |
| --- | --- |
| AEGM | Atrial electrogram |
| AF | Atrial fibrillation |
| AFL | Atrial flutter |
| AP | Atrial pace |
| AS | Atrial sense |
| AV | Atrial-ventricular |
| ICD | Implantable cardioverter-defibrillator |
| IEGM | Intracardiac electrogram |

-continued

| Term | Description |
| --- | --- |
| PAC | Premature atrial contraction |
| PVC | Premature ventricular contraction |
| RA | Right atrium |
| RV | Right ventricle |
| SEA | Subcutaneous electrode array |
| SECG | Surface electrocardiogram |
| VEGM | Ventricular electrogram |
| VF | Ventricular fibrillation |
| VFL | Ventricular flutter |
| VP | Ventricular pace |
| VS | Ventricular sense |

The present invention is directed to a dual-chamber (RA-RV), three-chamber (BiA-RV, or RA-BiV), or four-chamber (BiA-BiV) implantable cardiac device including pacemakers, defibrillators and cardioverters, which stimulate cardiac tissue electrically to control the patient's heart rhythm.

According to this invention, a far-field intra-atrial electrogram (AEGM) and a far-field intra-ventricular electrogram (VEGM) are independently filtered, scaled, and then summed to form a composite far-field electrogram.

Pacing spikes that are adaptive to the pacing amplitude and polarity are preferably added to generate a Lead-Free ECG. Additionally, event-dependent filters can be applied to further improve the morphological features of the Lead-Free ECG. The Lead-Free ECG can be synthesized in real-time in the implant device, or transmitted via telemetry to the programmer for display, or transmitted to the remote service center through Home Monitoring technology.

In accordance with the present invention, the morphological features of the Lead-Free ECG are highly compatible with the measured SECG. Clinically relevant cardiac timing and rhythm information are faithfully preserved. The algorithm provides flexibility to adjust atrial and ventricular filters independently. Moreover, the Lead-Free ECG algorithm provides flexibility to adjust atrial and ventricular gain factors independently and automatically.

According to the invention, the object is achieved by a heart stimulation device comprising:

an atrial far-field sensing stage that is connectable or connected to an electrode lead having at least one atrial sensing electrode for intra-atrial placement, wherein the atrial far-field sensing stage is adapted to process electric signals picked up via an atrial sensing electrode and to generate therefrom a far-field intra-atrial electrogram signal, a ventricular far-field sensing stage that is connectable or connected to an electrode lead having at least one ventricular sensing electrode for intra-ventricular placement, wherein the ventricular far-field sensing stage is adapted to process electric signals picked up via a ventricular sensing electrode and to generate therefrom a far-field intra-ventricular electrogram signal, a processing unit that is connected to said atrial far-field sensing stage and said ventricular far-field sensing stage and that is adapted to independently filter, scale, and then sum said filtered and scaled far-field intra-atrial electrogram and said filtered and scaled far-field intra-ventricular electrogram to form a composite far-field electrogram signal, and a telemetry unit that is at least indirectly connected to said processing unit and that is adapted to transmit a data signal representing said composite far-field electrogram signal.

Alternatively, the object of the invention is achieved by a heart stimulation system comprising an implantable heart stimulation device an atrial far-field sensing stage that is connectable or connected to an electrode lead having at least one atrial sensing electrode for intra-atrial placement, wherein the atrial far-field sensing stage is adapted to process electric signals picked up via an atrial sensing electrode and to generate therefrom a far-field intra-atrial electrogram signal, a ventricular far-field sensing stage that is connectable or connected to an electrode lead having at least one ventricular sensing electrode for intra-ventricular placement, wherein the ventricular far-field sensing stage is adapted to process electric signals picked up via a ventricular sensing electrode and to generate therefrom a far-field intra-ventricular electrogram signal, and a telemetry unit that is at least indirectly connected to said atrial far-field sensing stage and said ventricular far-field sensing stage to transmit a data signal representing said far-field intra-atrial electrogram signal and said far-field intra-ventricular electrogram signal, and an external device comprising a telemetry unit that is adapted to receive a data signal representing said far-field intra-atrial electrogram signal and said far-field intra-ventricular electrogram signal, and a processing unit that is connected to said external telemetry unit and that is adapted to process said far-field intra-atrial electrogram signal and said far-field intra-ventricular electrogram signal independently, wherein the processing includes filtering and scaling said far-field intra-atrial electrogram signal and said far-field intra-ventricular electrogram signal, and then to sum said filtered and scaled far-field intra-atrial electrogram signal and said filtered and scaled far-field intra-ventricular electrogram signal to form a composite far-field electrogram signal.

In the alternative embodiment, the processing unit is part of a service center instead of the implantable device. Thus, less processing power is needed in the implantable device. However, a higher transmission bandwidth for transmitting data from the implantable device to the service center is required.

In a typical embodiment, the heart stimulation device is an implantable cardioverter/defibrillator is connectable or connected to a shock lead providing a superior vena cava (SVC) shock coil and a right ventricular shock coil. The heart stimulation device further comprises a case providing an electrically conducting surface forming a case electrode. The atrial far-field sensing stage is adapted to be connected to said case electrode and said superior vena cava shock coil when picking up said far-field intra-atrial electrogram signal. The ventricular far-field sensing stage is adapted to be connected to said case electrode and said right ventricular shock coil when picking up said far-field intra-ventricular electrogram signal.

Alternatively, if no shock coils are available (as in pure pacemakers without ICD functionality) it is preferred if the heart stimulation device comprises a case providing an electrically conducting surface forming a case electrode. The atrial far-field sensing stage is adapted to be connected to said case electrode and an atrial ring electrode when picking up said far-field intra-atrial electrogram signal. The ventricular far-field sensing stage is adapted to be connected to said case electrode and right ventricular ring electrode when picking up said far-field intra-ventricular electrogram signal.

The heart stimulation device preferably comprises at least one stimulation pulse generator that is connectable or connected to an intra-ventricular stimulation electrode and that is adapted to generate a ventricular stimulation pulse for delivery via said intra-ventricular stimulation electrode. The heart stimulation device further comprises a control unit that is adapted to control said atrial far-field sensing stage and/or said ventricular far-field sensing stage to be blanked, when a ventricular stimulation pulse is delivered, and generate a VP marker signal when a ventricular stimulation pulse is delivered, and the processing unit is adapted to add a predefined VP spike template to said composite signal when receiving a VP marker signal.

Preferably, the processing unit is further adapted to modulate said VP spike template from a predefined VP template, so that its width is proportional to a measured VP pulse width, its height is proportional to a measured VP amplitude and further scaled based on the VP polarity. It is further preferred if the addition of said VP spike template to said composite far-field electrogram signal can be enabled or disabled by the programmable VP pulse ON/OFF switch The heart stimulation device preferably comprises at least one stimulation pulse generator that is connectable or connected to an intra-atrial stimulation electrode and that is adapted to generate an atrial stimulation pulse for delivery via said intra-atrial stimulation electrode. The heart stimulation device comprises a control unit that is adapted to control said atrial far-field sensing stage and/or said ventricular far-field sensing stage to be blanked, when an atrial stimulation pulse is delivered, and generate an AP marker signal when an atrial stimulation pulse is delivered, and the processing unit is adapted to add a predefined AP spike template to said composite signal when receiving an AP marker signal.

Preferably, the processing unit is further adapted to modulate said AP spike template from a predefined AP template, so that its width is proportional to a measured AP pulse width, its height is proportional to a measured AP amplitude and further scaled based on an AP polarity. It is further preferred if the addition of said AP spike template to said composite far-field electrogram signal can be enabled or disabled by the programmable AP pulse ON/OFF switch The scaling of said far-field intra-atrial or said far-field intra-ventricular electrogram preferably is defined by a gain factor that is adjustable.

In a preferred embodiment filtering of said far-field intra-atrial or said far-field intra-ventricular electrogram signal is performed by a filter having adjustable filter characteristics. Preferably, the filter comprises one or a cascade of filters with predefined filter characteristics, including filter type, corner frequency and phase delay.

The processing unit may comprise at least one second level filter for filtering the composite far-field electrogram signal. The processing unit may in particular comprise a plurality of second level filters second including optimized filters for AS, VS, AP, and VP events, in a window immediately following the respective event types, and a generic filter for the IEGM segment after the window.

The processing unit may also comprise a ventricular far-field electrogram amplifier and can be adapted to calculate the ratio of a desired R wave amplitude to a measured peak amplitude of a ventricular depolarization complex, and to adjust a ventricular gain factor to be applied by said ventricular far-field electrogram amplifier to a far-field intra-ventricular electrogram signal.

The processing unit can further be adapted to measure peak amplitudes of a ventricular depolarization complex and/or to measure an average of absolute peak amplitudes of a predetermined number of latest multiple VS complexes According to a preferred embodiment, the processing unit comprises an atrial far-field electrogram amplifier and is adapted to calculate the ratio of a desired P wave amplitude to a measured peak amplitude of an atrial depolarization complex, and to adjust an atrial gain factor to be applied by said atrial far-field electrogram amplifier to a far-field intra-atrial electrogram signal. It is further preferred if the processing unit is adapted to measure peak amplitudes of the atrial depolarization complex and/or to measure an average of absolute peak amplitude of a predetermined number of latest multiple AS complexes.

The processing unit may further be adapted to perform said measurement upon user's command during device implant or follow-up.

A further preferred arrangement is a pacemaker or ICD system comprising:
- an implantable device that sense and pace the patient's heart;
- an external programmer device that interrogate and program the implant device;
- an atrial lead for sensing of far-field AEGM;
- a ventricular lead for sensing of far-field VEGM;
- a wide-band channel for synthesizing Lead-free ECG in real-time in the implant device;
- a telemetry unit that transfer the Lead-free ECG channel to the external programmer or external portable device that links to remote service center through wired or wireless network, or transfer the far-field AEGM and the far-field VEGM to the external programmer to synthesize the Lead-free ECG;
- a wired or wireless network that transfer the Lead-free ECG channel to the remote service center, or transfer the far-field AEGM and far-field VEGM to the remote service center to synthesize the Lead-free ECG.

In such arrangement. the external programmer or external portable device preferably comprises:
- means to interrogate and receive the telemetry Lead-free ECG channel, or the far-field AEGM and far-field VEGM from the implant device;
- means to transmit the Lead-free ECG channel, or the far-field AEGM and far-field VEGM to the remote service center via Home Monitoring network;
- means to generate, plot and print the Lead-free ECG in a graphical user interface;
- means to provide a user-interface to allow user to independently select the atrial and/or ventricular filters;
- means to provide a user-interface to allow user to independently select the atrial and/or ventricular gain factors;
- a user-interface to allow user to independently select the desired P and/or R wave peak amplitudes;
- a user-interface to allow user to independently select the desired AP template and VP template;
- a user-interface to allow user to independently select the polarity attenuation factor for AP and VP;
- a user-interface to allow user to independently turn ON or OFF of the AP spike and VP spike in the Lead-free ECG.
- means to transmit the programmed parameters to the implant device.

In such arrangement, the remote service center preferably comprises:
- means to receive the Lead-free ECG channel, or the far-field AEGM and far-field VEGM transmitted by the device to the Home Monitoring network;
- means to generate, plot, and print the Lead-free ECG in a graphical user interface;
- means to transmit the Lead-free ECG to the attending physician or designated health practitioner via telephonic network or internet;
- means to provide a user-interface to allow user to independently program and select the atrial and/or ventricular filters (for synthesizing Lead-free ECG in the remote service center from the transmitted far-field AEGM and far-field VEGM);

means to provide a user-interface to allow user to independently program and select the atrial and/or ventricular gain factors (for synthesizing Lead-free ECG in the remote service center from the transmitted far-field AEGM and far-field VEGM);

a user-interface to allow user to independently program and select the desired P and/or R wave peak amplitudes (for synthesizing Lead-free ECG in the remote service center from the transmitted far-field AEGM and far-field VEGM);

a user-interface to allow user to independently program and select the desired AP template and VP template (for synthesizing Lead-free ECG in the remote service center from the transmitted far-field AEGM and far-field VEGM);

a user-interface to allow user to independently program and select the polarity attenuation factor for AP and VP (for synthesizing Lead-free ECG in the remote service center from the transmitted far-field AEGM and far-field VEGM);

a user-interface to allow user to independently turn ON or OFF of the AP spike and VP spike in the Lead-free ECG (for synthesizing Lead-free ECG in the remote service center from the transmitted far-field AEGM and far-field VEGM).

Another preferred arrangement to synthesize the Lead-free ECG by generating a composite far-field electrogram comprises:

means to measure the far-field AEGM;
means to measure the far-field VEGM;
means to obtain the sense and pace event markers;
means to apply blanking window to block the pacing artifacts from the AEGM and VEGM after AP and VP events;
means to independently adjust the atrial and ventricular filters;
means to independently adjust the atrial and ventricular gain factors;
means to automatically determine the atrial and ventricular gain factors;
means to filter the far-field AEGM;
means to filter the far-field VEGM;
means to scale the far-field AEGM;
means to scale the far-field VEGM;
means to generate a modulated AP spike following an AP;
means to generate a modulated VP spike following a VP;
means to form a composite signal from the filtered and scaled AEGM, the filtered and scaled VEGM, the modulated AP spike, and the modulated VP spike;
means to further filter the composite signal through a second layer filters that are dependent on the event types.

Another solution to the object of the invention is a method for generating an electrogram signal, that comprises the steps:

Picking up a far-field intra-atrial electrogram
simultaneously picking up a far-field intra-ventricular electrogram,
filtering said far-field intra-atrial electrogram
independently filtering said far-field intra-ventricular electrogram,
Scaling said far-field intra-atrial electrogram and/or said far-field intra-ventricular electrogram Summing said filtered and amplified far-field intra-atrial electrogram and said filtered and amplified far-field intra-ventricular electrogram, thus creating a composite far-field electrogram.

It is to be appreciated that features of preferred embodiments of the invention may be combined in any useful manner thus arriving at further preferred embodiments of the invention not explicitly mentioned in this disclosure.

The details of the Lead-Free ECG feature can be understood from the following drawings and the corresponding text descriptions.

BRIEF DESCRIPTION OF THE DRAWINGS

The foregoing and other objects, advantages and novel features of the present invention can be understood and appreciated by reference to the following detailed description of the invention, taken in conjunction the accompanying drawings, in which.

DETAILED DESCRIPTION OF THE INVENTION

Figure 1:
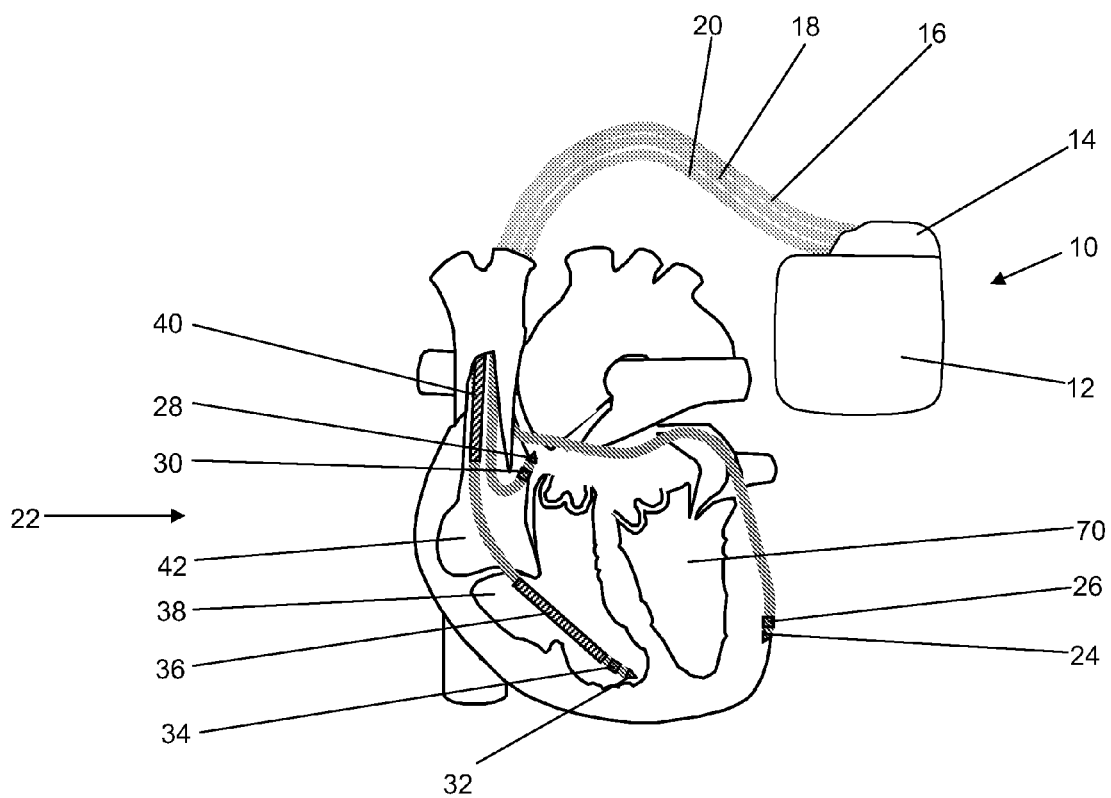
FIG. 1 illustrates the heart stimulator connected to electrode leads that are placed in a heart together with an external device.

From FIG. 1 it is apparent that stimulator 10 comprises a case 12 and header 14.

The heart stimulator 10 is connected to three electrode leads, namely a right ventricular electrode lead for 16, a right atrial electrode lead 18 and a left ventricular electrode lead 20.

The left ventricular electrode lead 20 is designed to pass through the coronary sinus, of heart 22. A typical electrode suitable for use with heart stimulator 10 is the electrode lead Corox+ UP/BB by the applicant. Left ventricular electrode lead 20 comprises a left ventricular tip electrode 24 at the distal end of a left ventricular electrode lead 20 and a left ventricular ring electrode 26.

Atrial electrode lead 18 comprises a right atrial tip electrode 28 at the distal end of right atrial electrode lead 18 and a right atrial ring electrode 30.

The right ventricular electrode lead 16 comprises right ventricular tip electrode 32 at the distal end of right ventricular electrode lead 16 and a right ventricular ring electrode 34.

In order to illustrate that heart stimulator 10 may be adapted to act as an implantable cardioverter/defibrillator (ICD) ventricular electrode lead 16 also exhibits a ventricular shock coil 36 for the delivery of defibrillation shocks to right ventricle 38 of heart 22 and a superior vena cava (SVC) shock coil 40 for the delivery of defibrillation shocks to a right atrium 42 of heart 22.

Each electrode and shock coil of electrode leads 16 to 20 is separately connected to an electric circuit enclosed by case 12 of heart stimulator 10 by way of electrical contacts of a plug (not shown) at the proximal end of each electrode lead 16 to 20 and corresponding contacts (not shown) in header 14 of heart stimulator 10.

Figure 2:
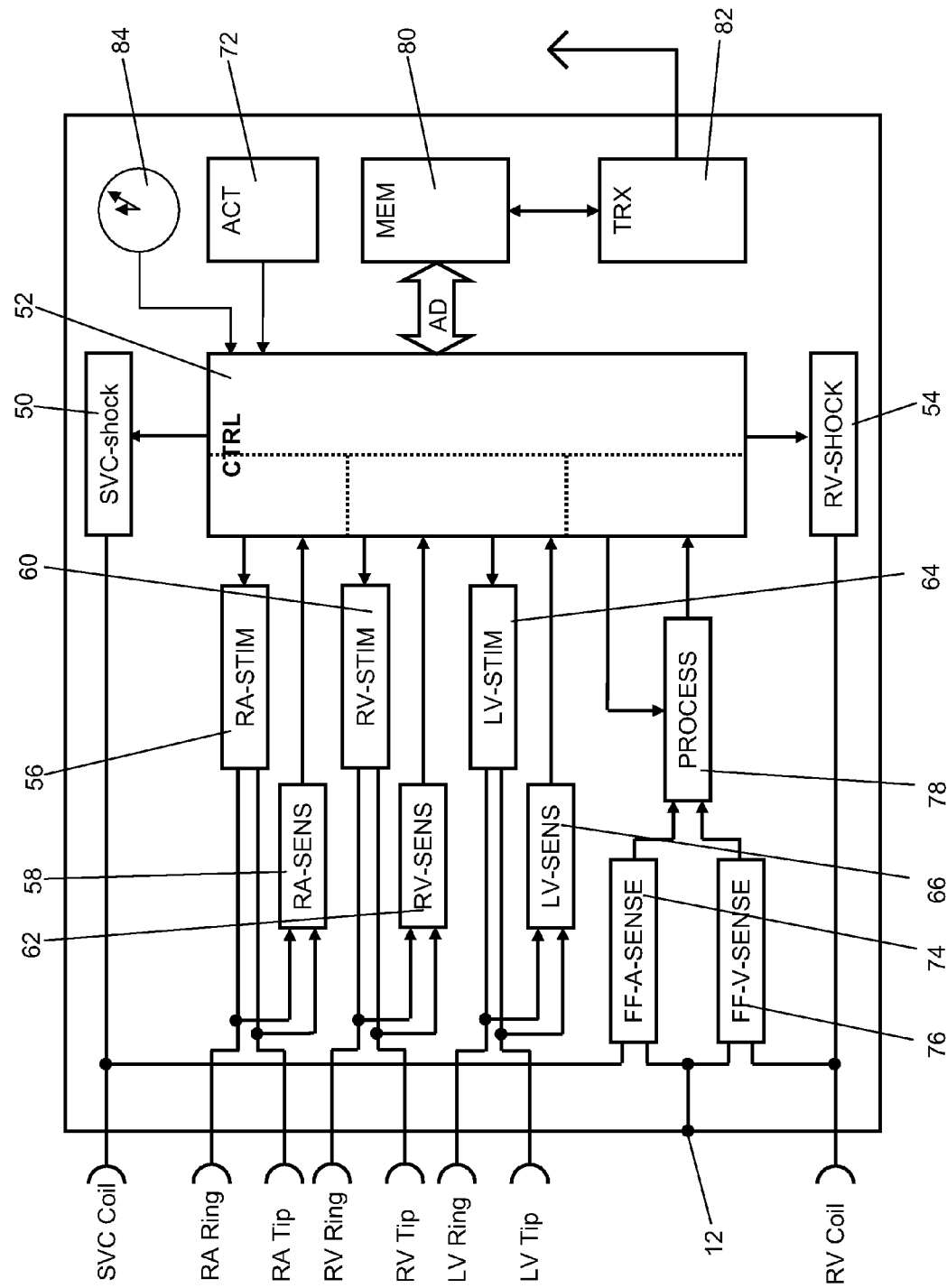
FIG. 2 shows a schematic block diagram of the heart stimulator of FIG. 1.

Now refer to FIG. 2. SVC shock coil 40 is connected to right atrial shock generator 50 that is controlled by a control unit 52 of heart stimulator 10.

Similarly, right ventricular shock coil 36 is connected to a right ventricular shock generator 54 that is also connected to control unit 52.

Right atrial tip electrode 28 and right atrial ring electrode 30 are both connected to a right atrial stimulation pulse generator 56 and a right atrial sensing stage 58 that internally both connected to control unit 52.

Right atrial stimulation pulse generator 56 is adapted to generate atrial stimulation pulses of sufficient strength to cause an excitation of atrial myocardium by an electrical pulse delivered via right atrial tip electrode 28 and right atrial ring electrode 30. Preferably, means are provided to adapt the right atrial stimulation pulse strength to the stimulation threshold in the right atrium.

Right atrial sensing stage 58 is adapted to pick up myocardial potentials indicating an intrinsic atrial excitation that corresponds to a natural atrial contraction. By way of right atrial tip electrode 28, it is possible to stimulate the right atrium 42 of heart 22 in a demand mode wherein a right atrial stimulation pulse is inhibited if an intrinsic atrial event (intrinsic atrial excitation) is sensed by right atrial sensing stage 58 prior to expiration of an atrial escape interval.

In a similar manner, right ventricular ring electrode 34 and right ventricular tip electrode 32 are connected to right ventricular stimulation pulse generator 60 and to a right ventricular sensing stage 62 that in turn are connected to control unit 52. By way of right ventricular tip electrode 32, right ventricular ring electrode 34, right ventricular stimulation generator 60 and right ventricular sensing stage 62, right ventricular stimulation pulses can be delivered in a demand mode to the right ventricle 38 of heart 22.

In the same way left ventricular tip electrode 24 and left ventricular ring electrode 26 are connected to the left ventricular stimulation pulse generator 64 and the left ventricular sensing stage 66 that internally connected to control unit 52 and that allow for stimulating a left ventricle 70 of heart 22.

Triggering and inhibition of delivery of stimulation pulses to the right atrium, the right ventricle or the left ventricle is controlled by control unit 52, in a manner known to the man skilled in the art. The timing that schedules delivery of stimulation pulses if needed is controlled by a number of intervals that at least partly may depend on a hemodynamic demand of a patient that is sensed by means of an activity sensor 72 that is connected to control unit 52. Activity sensor 72 allows for rate adaptive pacing wherein a pacing rate (the rate of consecutive ventricular stimulation pulses for a duration of consecutive atrial stimulation pulses) depends on a physiological demand of a patient that is sensed by a way of activity sensor 72.

For the purpose of measurement of a far-field intra-atrial electrogram (AEGM) and a far-field intra-ventricular electrogram (VEGM) a far-field atrial sensing stage 74 and a far-field ventricular sensing stage 76, respectively, are provided. The far-field atrial sensing stage 74 is connected to a case electrode that is formed by at least an electrically conducting part of case 12 of the heart stimulator 10 and to the SVC coil electrode 40.

The far-field ventricular sensing stage 76 is also connected to the case electrode formed by a case 12 of heart stimulator 10 and to the right ventricular coil electrode 36. Both, far-field atrial sensing stage 74 and far-field ventricular sensing stage 76, are adapted to pick up far-field intracardiac electrograms and to generate electrogram signals that are fed to a processing unit 78. Processing unit 78 is adapted to filter and scale each electrogram signal received from either the far-field atrial sensing stage 74 or the far-field ventricular sensing stage 76 or both independently from each other and to sum the resulting filtered and scaled electrogram signals in order to generate the composite far-field electrogram signal.

Figure 3:
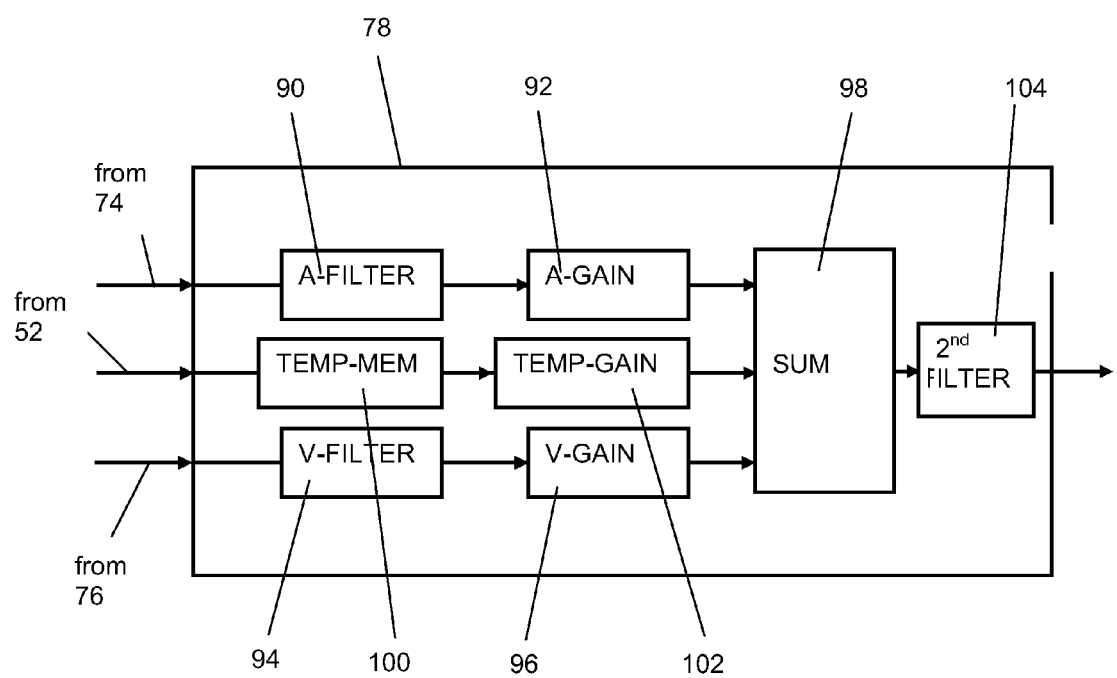
FIG. 3 shows a schematic block diagram of a processing unit according to the invention.

As it is apparent from FIG. 3, processing unit 78 comprises at least an atrial far-field electrogram filter 90 and an atrial far-field electrogram amplifier 92 that at least indirectly is connected to the atrial far-field electrogram filter 90. The atrial far-field electrogram filter 90 receives signal from the far-field atrial sensing stage 74.

Similarly, a ventricular far-field electrogram filter 94 is provided, receiving an output signal from far-field ventricular sensing stage 76. Far-field electrogram amplifier 96 is connected to the ventricular far-field electrogram filter 94 and is adapted to scale the filtered far-field electrogram signal by a gain factor, that may be larger or smaller than or equal to zero.

Both, atrial far-field electrogram amplifier 92 and ventricular far-field electrogram amplifier 96 are connected to a summing stage 98. Summing stage 98 is adapted to sum the synchronized output signals of the atrial far-field electrogram amplifier 92 and the ventricular far-field electrogram amplifier 96 to thus generate a composite far-field electrogram signal. This composite far-field electrogram signal may be directly fed to a memory 80 or telemetry unit 82 or to control unit 52.

Since the far-field atrial sensing stage 74 and the far-field ventricular sensing stage 76 preferably are blanked during delivery of an atrial and/or ventricular stimulation pulse, no far-field atrial electrogram signal or far-field ventricular electrogram signal can be picked up during blanking of the respective far-field sensing stage 74 or 76. In order to have the composite far-field electrogram signal more closely resemble a true surface electrogram signal typical signals appearing in a true surface electrogram signal during atrial or ventricular stimulation are added to the composite far-field electrogram signal. For this purpose, a template memory 100 is provided comprising templates for the case of atrial stimulation and for the case of ventricular stimulation. The template memory 100 is connected to a template amplifier 102 that can scale the template stored in template memory 100 as necessary. Addition of a template to the composite far-field electrogram signal is triggered by receiving either an atrial marker signal or a ventricular marker signal from control unit 52. Control unit 52 generates an atrial marker signal whenever an atrial stimulation pulse is triggered. Likewise, control unit 52 generates a ventricular marker signal whenever a ventricular stimulation pulse is triggered.

For further processing of the composite far-field electrogram signal, second level filters 104 are provided that are connected to the output off summing stage 98. The second level filters 98 include optimized filters for AS, VS, AP, and VP events, in a window immediately following the respective event types, and a generic filter for the IEGM segment after the window.

Figure 4:
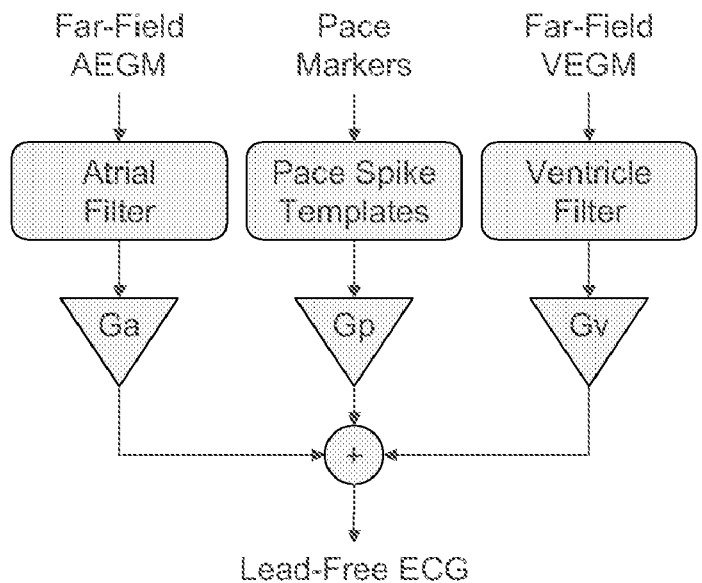
FIG. 4 is a schematic block diagram illustrating the composite far-field method for Lead-Free ECG.

Refer to FIG. 4. According to this invention, the far-field atrial electrogram (AEGM) and the far-field ventricular electrogram (VEGM) are independently filtered, gained (that is, scaled by a gain-factor), and then summed to form the composite far-field signal. In other words, the Lead-Free ECG output can be considered as the weighted sum of the filtered far-field AEGM and the filtered far-field VEGM. The rational for this approach is based on the fact that the P-QRS-T waves in SECG is the far-field presentation of the composite atrial and ventricular electrical signals over the body surface. Therefore, other composite signals that include far-field atrial and ventricular components may present similar characteristics as the SECG.

The far-field AEGM can be recorded by the implant device by using 'RA tip-Case', or 'RA ring-Case', or 'SVC coil-Case' configuration. Likewise, the far-field VEGM can be recorded by the implant device using 'RV tip-Case', or 'RV ring-Case', or 'RV coil-Case' sense configuration. Theoretically, any combination of far-field AEGM and far-field VEGM may form the composite far-field signal. However, the tip-case sense configuration may be subject to undesirable after-potentials and polarization effects, while the coil-case sense configuration is limited to the shock lead and ICD device only. Therefore, for the general purpose of Lead-Free ECG, the 'RA ring-Case' AEGM and 'RV ring-Case' VEGM are preferred choices to form the composite far-field signal.

In a preferred embodiment, the Lead-Free ECG is synthesized in real-time in the implant device. During implantation and follow-up, the device-generated Lead-Free ECG can be transmitted to the programmer for display. In another embodiment, the device-generated Lead-Free ECG is transmitted to the remote service center through Home Monitoring wireless network.

According to this invention, the far-field AEGM is processed through an atrial filter or a cascade of atrial filters to remove the undesired high frequency noise and low frequency baseline drifting, and to add a phase delay between the AEGM complexes and the corresponding P waves. In a typical embodiment, a band pass filter with low cut-off 4 Hz and high cut-off 32 Hz, and a linear phase delay of 20 ms is used. Similarly, the far-field VEGM is processed through a ventricle filter or a cascade of ventricle filters to remove the undesired high frequency noise and low frequency baseline drifting. In a typical embodiment, a band pass filter with low cut-off 4 Hz and high cut-off 64 Hz, and a linear phase delay of 10 ms is used.

According to this invention, a user-interface is provided in the programmer that allows the user to independently modify the atrial and ventricular filter, including but not limited to, the filter type, the filter order or phase delay, and the filter corner frequencies, as known in the art. The flexibility to adjust atrial and ventricular filters independently is important because the optimal filter characteristics from atrial and ventricular IEGM channels to SECG could be substantially different due to different volume conduction pathways.

The filtered far-field AEGM is scaled by an atrial gain factor. For 'RA ring-Case' configuration, a negative gain factor converts the sense polarity to Case (+) and RA ring (−). This usually leads to positive P waves in the Lead-Free ECG, based on the observation that atrial depolarization often has negative deflections in this sense configuration. Similarly, the filtered far-field VEGM is scaled by a ventricle gain factor. For 'RV ring-Case' configuration, a negative gain factor converts the sense polarity to Case (+) and RV ring (−). This generally leads to positive R wave in the Lead-Free ECG, because the ventricle depolarization in this configuration often has negative deflections.

According to this invention, user can independently adjust the atrial and ventricular gain factors through the programmer. This feature is important because it can compensate for the difference between AEGM and VEGM amplitudes, which depend on lead location, sensing circuit properties, lead-tissue interface, among many other factors. In one embodiment, a user-interface is provided in the programmer that allows the user to independently modify the atrial and ventricular gain factors. In a second embodiment, the atrial and ventricular gain factors can be automatically determined as described below. Yet in a third embodiment, the automatically determined gain factors can be further scaled by a different set of gain factors that can be set by the user through a user-interface provided by the programmer.

The independently filtered and gained far-field AEGM and VEGM are summed to generate the composite ECG, which is free of pace pulses due to pace blanking of the AEGM and VEGM as known in the art. According to this invention, following an AP or VP event marker, a predefined AP or VP spike template is modulated and added to the composite ECG to represent the pacing artifact. Adding spikes after paces will make the composite IEGM more reasonably resemble the appearance of the SECG. In addition, the amplitude of the pace spikes can also provide a visual cue of the pacing amplitude, for example, during the pacing threshold search.

In one embodiment, the AP and VP spike templates are stored in the programmer and remote service center. The composite IEGM that is free of pacing artifact is transmitted to the programmer or remote service center through telemetry or Home Monitoring, and then the AP and VP spikes are added to generate the Lead-Free ECG. In another embodiment, the AP and VP spike templates are stored in the memory of the implant device. The AP and VP spikes are directly added to the composite IEGM by the implant device to generate the Lead-Free ECG, which is then transmitted to the programmer or remote service center through telemetry or Home Monitoring.

It is noted that when the AEGM and VEGM have the same filter settings but opposite gain factors, the resulting composite IEGM is related to the difference between AEGM and VEGM, or equivalent to the filtered and gained 'RA ring-RV ring' signal. Therefore, the 'RA ring-RV ring' sense configuration can be considered as a special case of the composite far-field method. In general, the weighted sum of the far-field AEGM and VEGM (as disclosed in this invention) is superior to the differential 'RA ring-RV ring' sensing, because: (1) The former provides flexibility to adjust atrial and ventricular filters independently. (2) The former provides flexibility to adjust atrial and ventricular gains independently. (3) From physiological point of view, SECG is the sum, not the difference of the atrial and ventricular components. (4) The ventricular complex in 'RV ring-Case' VEGM usually has the same phase polarity as its far-field component in the 'RA ring-Case' AEGM. Therefore, 'RA ring-RV ring' sensing tends to reduce the signal amplitude of the R wave, whereas summed far-field signal tends to increase the amplitude of the R wave. Therefore, the differential far-field signal tends to have much smaller signal to noise ratio than the summed far-field signal. Moreover, the far-field T wave in AEGM is usually much smaller compared to the far-field R wave in AEGM, thus the T/R amplitude ratio tends to be larger in differential sensing than in the summed far-field signal. This can lead to undesirable large amplitude T wave (particularly after VP) in the 'RA ring-RV ring' sensing.

Figure 5:
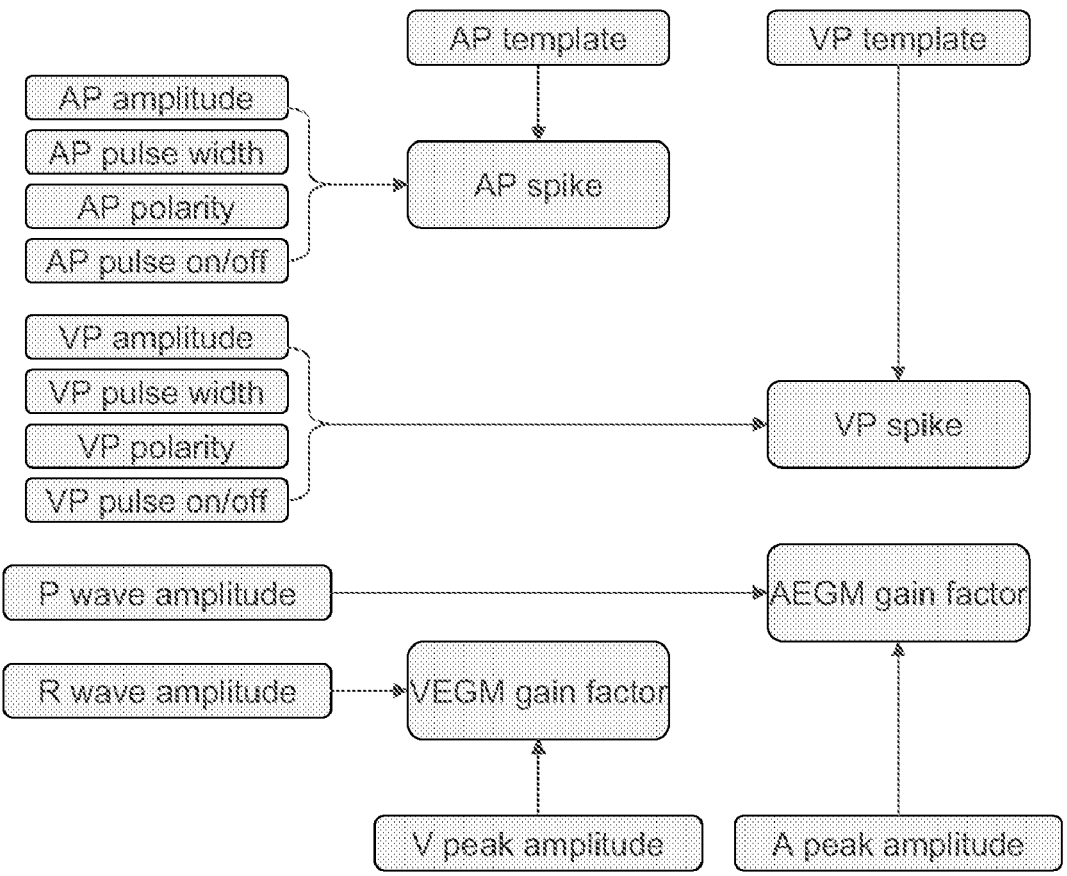
FIG. 5 is a schematic block diagram illustrating the automatic determination of the pacing pulses and channel gains.

Refer to FIG. 5. The atrial and ventricular gain factor can be automatically determined. According to this invention, the atrial gain factor is automatically calculated as the ratio of the desired P wave amplitude to the measured peak amplitude of the atrial depolarization complex. Likewise, the ventricle gain factor is automatically calculated as the ratio of the desired R wave amplitude to the measured peak amplitude of the ventricle depolarization complex. In a preferred embodiment, a user-interface is provided in the programmer that allows the user to independently set the desired P wave amplitude and the desired R wave amplitude. The peak amplitudes of the AEGM and VEGM are measured upon user's demand, preferably during device implant or follow-up. In a typical embodiment, the AEGM peak amplitude is measured as the average of the absolute peak amplitudes of the latest four AS complexes. Similarly, the VEGM peak amplitude is measured as the average of the absolute peak amplitudes of the latest four VS complexes.

As described above, following an AP or VP event marker, a predefined AP or VP spike is added to the output to represent the pacing artifact that is commonly observed in the SECG. As illustrated in FIG. 5, the AP spike is modulated from the predefined AP pulse template, by taking into account following factors: (1) AP amplitude, (2) AP pulse width, (3) AP polarity, and (4) a user-programmable AP pulse ON/OFF switch. Similarly, the VP spike is modulated from the predefined VP pulse template, by taking into account following factors: (1) VP amplitude, (2) VP pulse width, (3) VP polarity, and (4) a user-programmable VP pulse ON/OFF switch.

In a typical embodiment, the predefined AP pulse template represents the 'normalized' artifact that would be seen in the SECG after a unipolar AP with fixed amplitude and pulse width. The added AP spike is modulated (via scaling, up or down sampling) from the AP pulse template, so that its width is proportional to the AP pulse width, while its height is proportional to the AP amplitude and further scaled based on the AP polarity. Furthermore, the user can enable or disable the addition of the AP spike to the composite IEGM by programming the AP pulse ON/OFF switch (preferred default setting: ON).

Likewise, the predefined VP pulse template represents the 'normalized' artifact that would be seen in the SECG after a unipolar VP with fixed amplitude and pulse width. The added VP spike is modulated (via scaling, up or down sampling) from the VP pulse template, so that its width is proportional to the VP pulse width, while its height is proportional to the VP amplitude and further scaled based on the VP polarity. Furthermore, the user can enable or disable the addition of the VP spike to the composite IEGM by programming the VP pulse ON/OFF switch (preferred default setting: ON).

For example, assume the AP pulse template corresponds to a unipolar AP with 2.4V amplitude and 0.4 ms pulse width. Then for a unipolar AP with 4.8V amplitude and 0.2 ms pulse width, the added AP spike will be modulated from the AP pulse template by doubling its amplitude while shrinking its width by half. For a bipolar AP, the AP spike amplitude is further scaled by an attenuation factor that is user-programmable with range from 0 to 1, based on the observation that the bipolar AP usually shows smaller pacing artifact on the SECG than the unipolar AP.

In another example, assume the VP pulse template corresponds to a unipolar VP with 2.4V amplitude and 0.4 ms pulse width. Then for a unipolar VP with 1.2V amplitude and 0.8 ms pulse width, the added VP spike will be modulated from the VP pulse template by reducing its amplitude by half while doubling its width. For a bipolar VP, the VP spike amplitude is further scaled by an attenuation factor that is user-programmable with range from 0 to 1, based on the observation that the bipolar VP usually shows smaller pacing artifact on the SECG than the unipolar VP.

Figure 6:
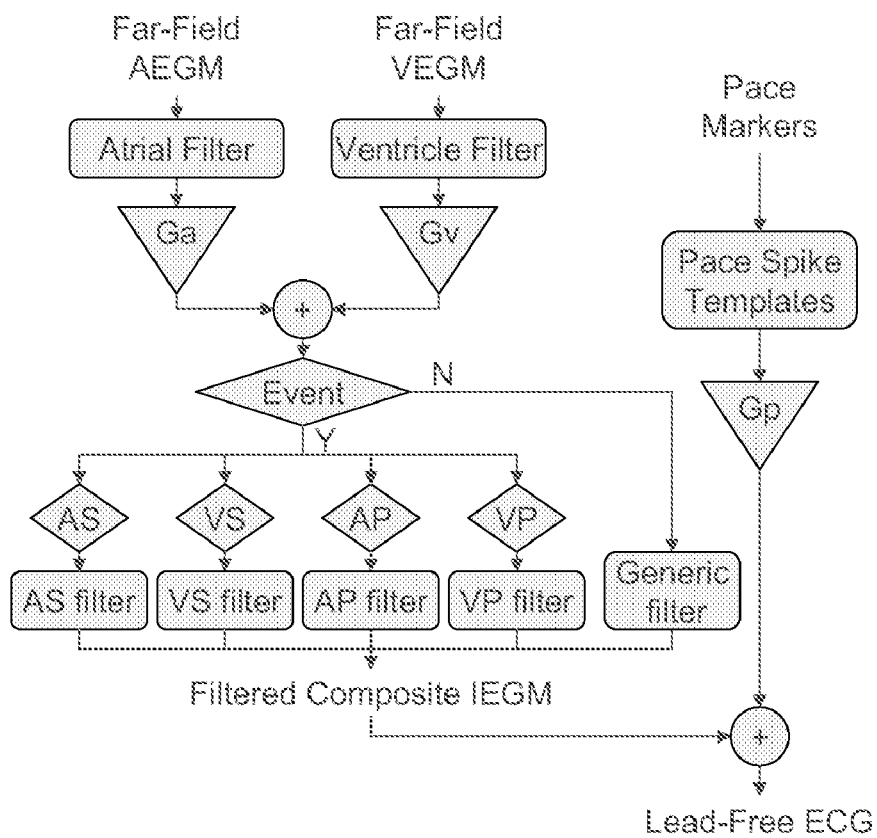
FIG. 6 is a schematic block diagram illustrating the extended composite far-field method for Lead-Free ECG.

Now refer to FIG. 6. Similarly to the approach described in FIG. 4, the far-field AEGM and the far-field VEGM are respectively filtered and gained, and then summed to generate the composite IEGM. Thereafter, a second layer of event-dependent filters is applied. That is, an AS filter is applied following an AS event, a VS filters is applied following a VS event, an AP filter is applied following an AP event, and a VP filters is applied following a VP event. After a predefined window following the sensed or paced event, a generic (or no) filter is applied. The second-layer-filtered composite IEGM, added with pace pulses upon AP or VP markers, forms the Lead-free ECG. The benefit of adding the second layer filters is to generate output that more closely resembles the SECG morphology, because it is believed by the inventors that the optimal filter characteristics (including frequency spectrum and phase spectrum) could be substantially different for sensed events and paces events in atrial and ventricular channels. The AS, AP, VS, and VP filters can be predefined or user-programmable, or could be adaptive to each individual patient according to the method disclosed in a concurrent patent disclosure (see U.S. patent application Ser. No. 11/668,491).

In the following, FIGS. 7 to 18 show some typical examples of Lead-free ECG recorded in human subjects or swine models. In each figure, the 1st panel plots the far-field AEGM, and the 2nd panel plots the far-field VEGM. The measures SECG is shown in the 3rd panel, and the synthesized Lead-free ECG is shown in the 4th panel. The AP event markers are labelled by red dots in the AEGM, and the VP event markers are labelled by the red dots in the VEGM.

Figure 7:
FIG. 7 shows an example of Lead-Free ECG in AS-VS rhythm.

FIG. 7 shows an example of Lead-free ECG in AS-VS rhythm. Although not identical to the SECG, the Lead-free ECG shows distinctive P waves, QRS complexes, and T waves corresponding to those of the measured SECG. Thus important cardiac timing and rhythm information is well preserved in the Lead-free ECG.

Figure 8:
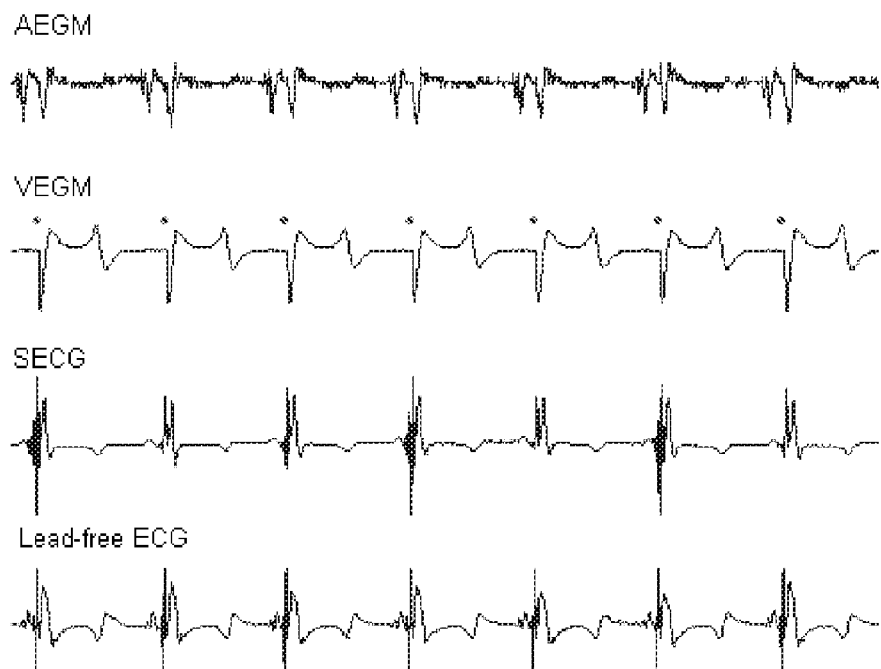
FIG. 8 shows an example of Lead-Free ECG in AS-VP rhythm.

FIG. 8 shows an example of Lead-free ECG in AS-VP rhythm (unipolar VP). Note that the unipolar VPs are associated with large pacing artifacts in the SECG. The Lead-free ECG clearly shows sensed P waves, and paced QRS complexes and T waves, corresponding to those of the measured SECG. Thus important cardiac timing and rhythm information is well preserved in the Lead-free ECG. Also note in this example, due to insufficient sampling frequency, the SECG shows non-uniform VP artifacts despite of uniform VP energy being delivered. On the other hand, the Lead-free ECG shows more desirable constant VP spikes.

Figure 9:
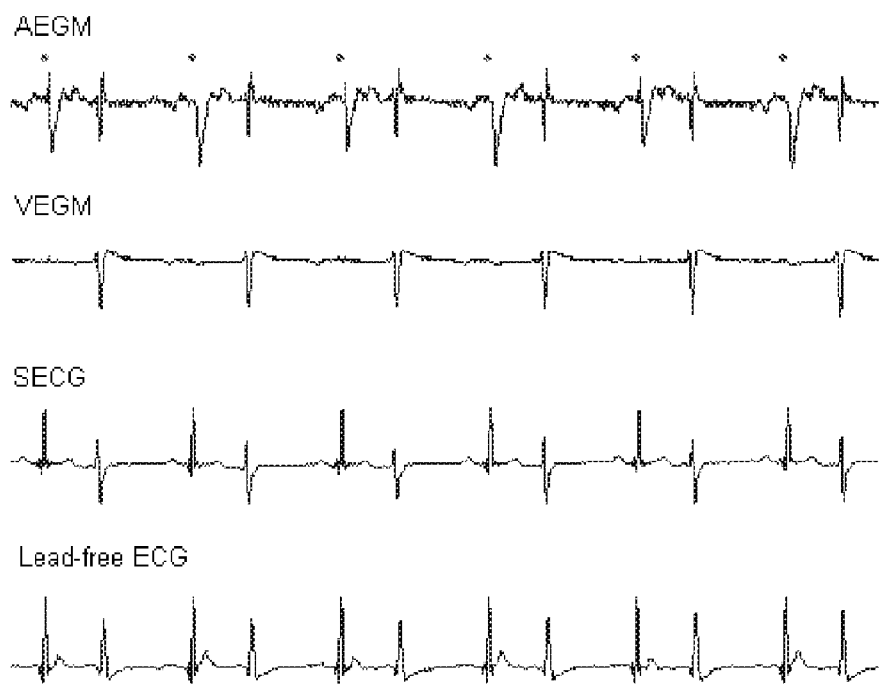
FIG. 9 shows an example of Lead-Free ECG in AP-VS rhythm.

FIG. 9 shows an example of Lead-free ECG in AP-VS rhythm (unipolar AP). Note that the unipolar APs are associated with large pacing artifacts in the SECG. The Lead-free ECG clearly shows paced P waves, and sensed QRS complexes and T waves, corresponding to those of the measured SECG. Thus important cardiac timing and rhythm information is well preserved in the Lead-free ECG.

Figure 10:
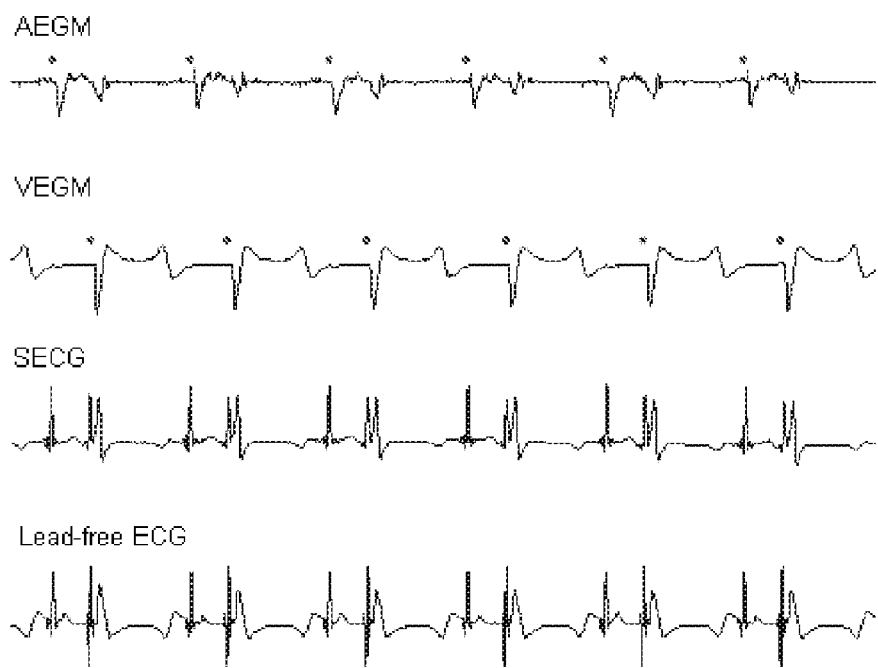
FIG. 10 shows an example of Lead-Free ECG in AP-VP rhythm.

FIG. 10 shows an example of Lead-free ECG in AP-VP rhythm (unipolar AP, unipolar VP). Note that the unipolar APs and VPs are associated with large pacing artifacts in the SECG. The Lead-free ECG clearly shows paced P waves, and paced QRS complexes and T waves, corresponding to those of the measured SECG. Thus important cardiac timing and rhythm information is well preserved in the Lead-free ECG.

Figure 11:
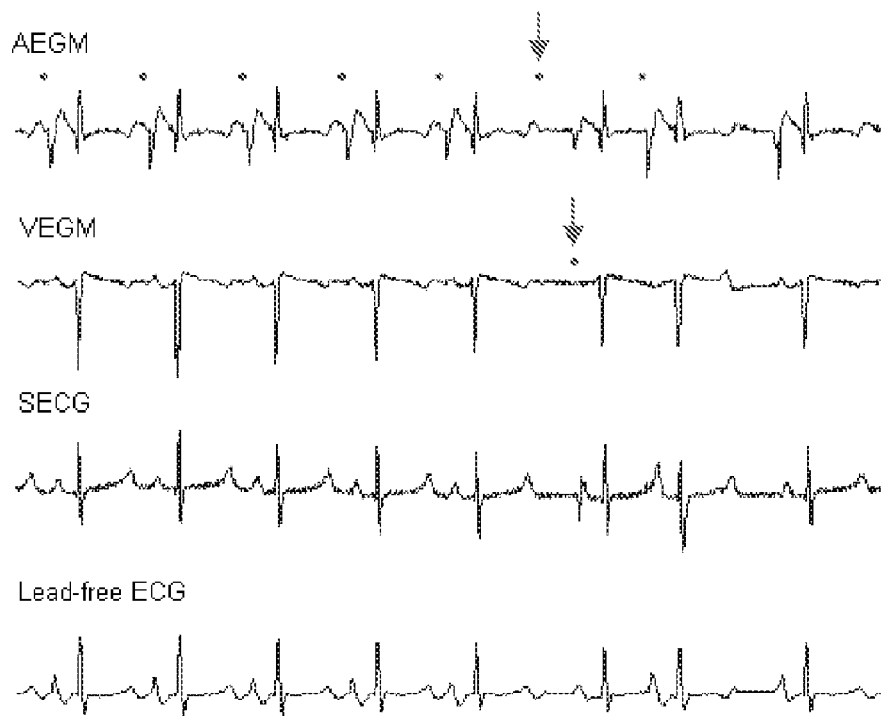
FIG. 11 shows an example of Lead-Free ECG with non-capture AP.

FIG. 11 shows an example of Lead-free ECG with non-capture AP and VP (bipolar AP, bipolar VP). Note that in this example, bipolar APs and VP did not elicit apparent pacing artifacts in SECG. A conducted VS follow each capture AP. The non-capture AP (marked by the downward arrow) is followed by an intrinsic P wave and conducted QRS complex, which results in VP non-capture (marked by the downward arrow). Non-capture AP and VP are evidenced by the absence of evoked response in the respective AEGM and VEGM. As expected, no P wave is seen in Lead-free ECG after the non-capture AP, and the conducted QRS complex following the non-capture AP has the same morphology as other sensed QRS complexes.

Figure 12:
FIG. 12 shows an example of Lead-Free ECG with non-capture VP.

FIG. 12 shows an example of Lead-free ECG with non-capture VPs (bipolar VP). The non-capture VPs (marked by the downward arrows) are evidenced by the absence of the evoked response in VEGM. A conducted QRS complex due to earlier atrial depolarization follows each non-capture VP. The Lead-free ECG clearly shows two distinct QRS-T morphologies corresponding to the capture VPs and the non-capture VPs, respectively.

Figure 13:
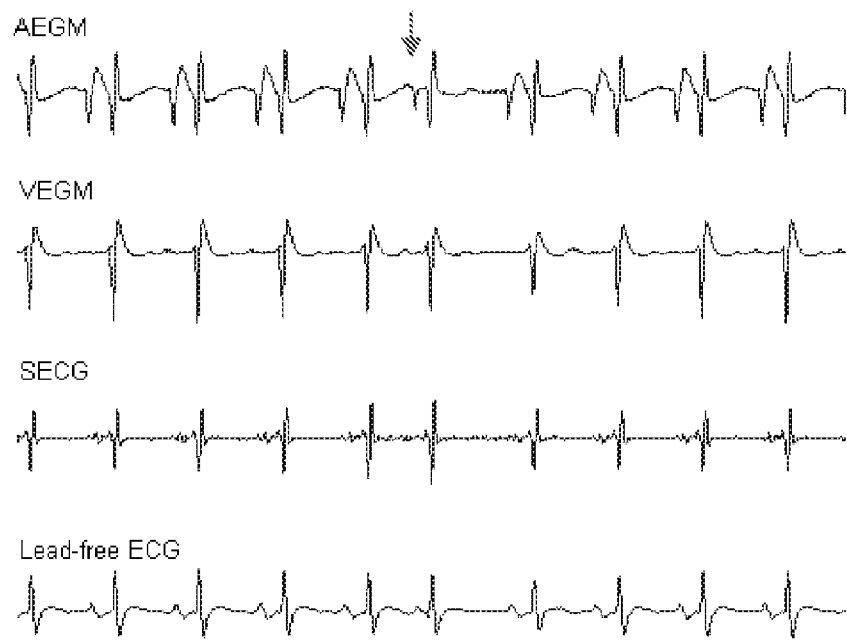
FIG. 13 shows an example of Lead-Free ECG with PAC.

FIG. 13 shows an example of Lead-free ECG with PAC. The ectopic atrial beat (marked by the downward arrow) can be easily identified in the Lead-free ECG—not only by the short atrial coupling interval, but also by the different morphology of the P wave. The conducted QRS complex following the PAC, however, shows similar morphology as other normally conducted QRS complexes.

Figure 14:
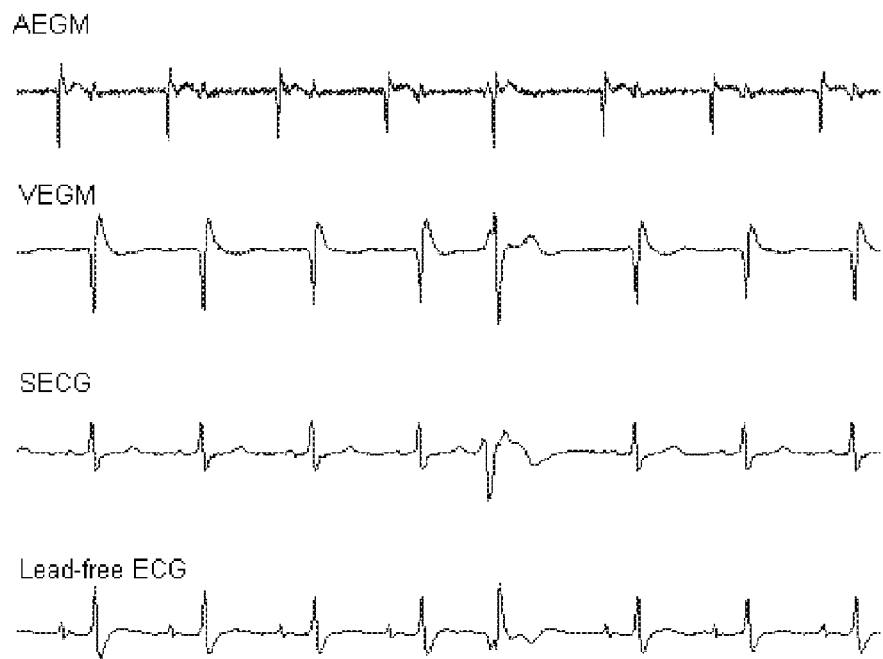
FIG. 14 shows an example of Lead-Free ECG with PVC.

FIG. 14 shows an example of Lead-free ECG with PVC. The ectopic ventricular beat is easily identifiable in the Lead-free ECG—not only by the short ventricular coupling interval, but also by the distinct waveform morphology of the QRS complex, which is not preceded by the P wave.

Figure 15:
FIG. 15 shows an example of Lead-Free ECG with AFL.

FIG. 15 shows an example of atrial flutter (AFL) rhythm. Note that the recorded SECG was contaminated by low-level noise, such that the flutter P waves were not clearly identified. On the other hand, the Lead-free ECG clearly shows flutter P waves that have one-to-one correspondence to the atrial depolarization complexes in the AEGM.

Figure 16:
FIG. 16 shows an example of Lead-Free ECG with AF.

FIG. 16 shows an example of atrial fibrillation (AF) rhythm. Note that although the fibrillatory P waves are difficult to be detected in the measured SECG, they are visually identifiable in the Lead-free ECG.

Figure 17:
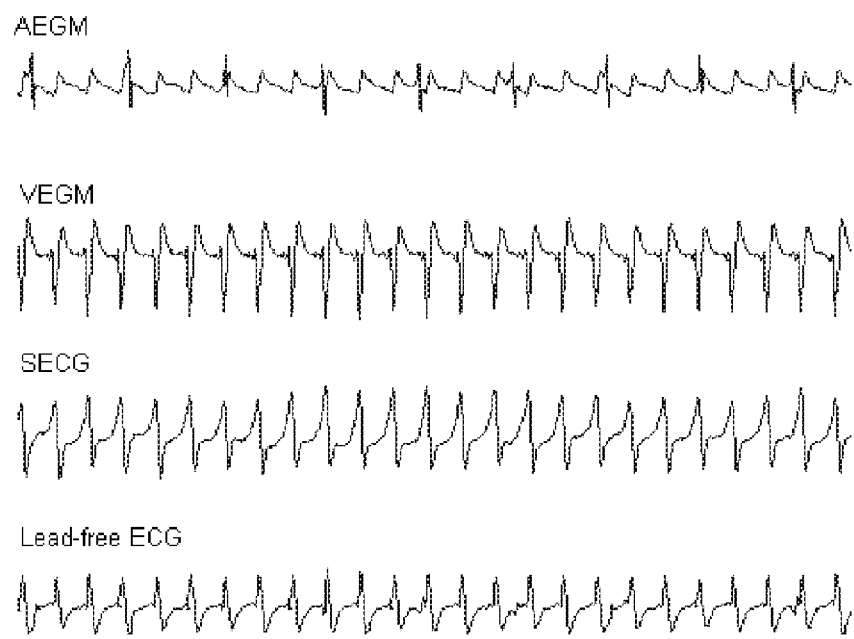
FIG. 17 shows an example of Lead-Free ECG with VFL.

FIG. 17 shows an example of ventricle flutter (VFL) rhythm. The Lead-free ECG morphology is comparable to that of the recorded SECG. Also note that the pattern of QRS morphology is consistent from beat to beat—an indication of monomorphic VT.

Figure 18:
FIG. 18 shows an example of Lead-Free ECG with VF.
Figure 18:
Figure 18:
Figure 18:

FIG. 18 shows an example of ventricle fibrillation (VF) rhythm. Again, the Lead-free ECG waveform is correlated with the SECG waveform, clearly preserves the rhythm information that is sufficient for diagnosis of the underlying VF activity.

Figure 19:
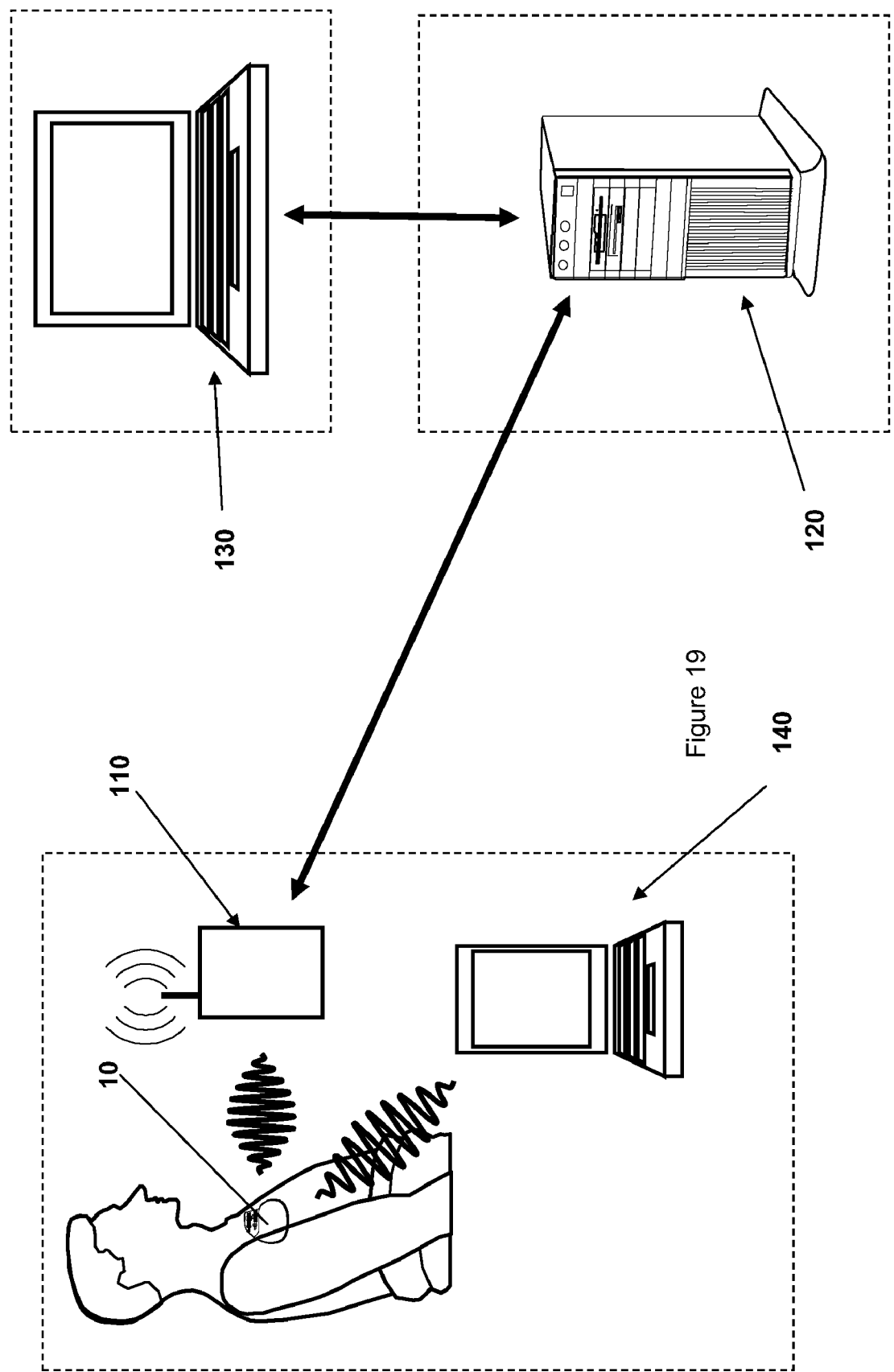
FIG. 19 illustrates an arrangement including a heart stimulator according to FIGS. 1 and 2 and a service center.

FIG. 19 shows an arrangement forming a heart stimulation system that is adapted to generate and display a far-field electrogram signal. The arrangement comprises a heart stimulator 10 that be identical to the heart stimulator 10 as illustrated in FIG. 1 to 3. Further, the arrangement comprises an external device 110, that comprises a telemetry unit for wireless data communication with the heart stimulator 10. The external device 110 is further connected to a service center 120 that in turn is connected to a computer terminal 130. The heart stimulator 10 is adapted to transmit data representing a composite far field electrogram signal wirelessly to the external device 110 that in turn forwards the data to service center 120. Service center 120 is adapted to generate a graphical user interface for displaying a graphical representation of the composite far-field electrogram signal data received from the heart stimulator 10 via external device 110. The graphical representation may be displayed on the screen of computer terminal 130. It is to be noted that computer terminal 130 can be an independent work station such as a laptop that is connected to the service center 120 via the internet.

In an alternative embodiment, the heart stimulator is adapted to simply pick up a far-field intra-atrial electrogram signal and a far-field intra-ventricular electrogram signal and to wirelessly transmit data representing these signals to external device 110. External device 110 forwards these data to service 120. In this case, service center 120 comprises a processing unit similar to processing unit 78 to filter and scale the intra-atrial and intra-ventricular far-field electrogram signals received from the heart stimulator. Thus computing workload is transferred from the heart stimulator to the service center. However, usually a higher band width for transmitting data from the heart stimulator to the service center is required.

For an immediate data exchange with the implantable heart stimulator 10 a programmer 140 may be provided. Programmer 140 is adapted to allow programming of the implantable heart stimulator 10 by a short range wireless data telecommunication connection. Programmer 140 may be adapted to receive data representing either a far-field intra-atrial electrogram signal and a far-field intra-ventricular electrogram signal or a composite far-field electrogram signal. In the first case, programmer 140 comprises a processing unit similar to processing unit 78 as shown in FIG. 3 for generating a composite far-field electrogram signal from the signals received from implantable heart stimulator 10. The programmer 140 further is adapted to display a graphical representation of the composite far field electrogram signal thus generated. Alternatively, programmer 140 may be adapted to directly receive a composite far-field electrogram signal from the implantable heart stimulator 10 that has been generated by the implantable heart stimulator 10. In that case, programmer 140 will generate and display a graphical representation of the composite far-field electrogram signal received from the implantable heart stimulator 10.

Although an exemplary embodiment of the present invention has been shown and described, it should be apparent to those of ordinary skill that a number of changes and modifications to the invention may be made without departing from the spirit and scope of the invention. This invention can readily be adapted to such devices by following the present teachings. All such changes, modifications and alterations should therefore be recognized as falling within the scope of the present invention.

What is claimed is:

1. A heart stimulation device comprising
    an atrial far-field sensing stage that is connectable or connected to a first electrode lead having at least one atrial sensing electrode for intra-atrial placement, wherein said atrial far-field sensing stage is configured to process electric signals picked up via said at least one atrial sensing electrode and to generate therefrom a far-field intra-atrial electrogram signal;
    a ventricular far-field sensing stage that is connectable or connected to a second electrode lead having at least one ventricular sensing electrode for intra-ventricular placement, wherein said ventricular far-field sensing stage is configured to process electric signals picked up via said at least one ventricular sensing electrode and to generate therefrom a far-field intra-ventricular electrogram signal;

a processing unit that is coupled with said atrial far-field sensing stage and said ventricular far-field sensing stage and that is configured to independently filter, scale, and then sum said filtered and scaled far-field intra-atrial electrogram and said filtered and scaled far-field intra-ventricular electrogram to form a composite far-field electrogram signal;

a telemetry unit that is at least indirectly connected to said processing unit and that is configured to transmit a data signal that represents said composite far-field electrogram signal;

wherein said heart stimulation device comprises at least one stimulation pulse generator that is connectable or connected to an intra-ventricular stimulation electrode and that is configured to generate a ventricular stimulation pulse that is delivered via said intra-ventricular stimulation electrode;

wherein said heart stimulation device comprises a control unit that is configured to control said atrial far-field sensing stage and/or said ventricular far-field sensing stage to be blanked, when said ventricular stimulation pulse is delivered, and generate a Ventricular Pace or VP marker signal when said ventricular stimulation pulse is delivered; and, wherein said processing unit is configured to add a predefined VP spike template to said composite far-field electrogram signal when said VP marker signal is received.

2. The heart stimulation device according to claim 1, wherein said heart stimulation device is an implantable cardioverter/defibrillator configured to be connected to a shock lead providing a superior vena cava or SVC shock coil and a right ventricular shock coil and wherein said heart stimulation device further comprises a case providing an electrically conducting surface that forms a case electrode and wherein said atrial far-field sensing stage is configured to be connected to said case electrode and said superior vena cava shock coil to pick up said far-field intra-atrial electrogram signal and wherein said ventricular far-field sensing stage is configured to be connected to said case electrode and said right ventricular shock coil to pick up said far-field intra-ventricular electrogram signal.

3. The heart stimulation device according to claim 1, wherein said heart stimulation device comprises a case that provides an electrically conducting surface that forms a case electrode and wherein said atrial far-field sensing stage is configured to be connected to said case electrode and an atrial ring electrode to pick up said far-field intra-atrial electrogram signal and wherein said ventricular far-field sensing stage is configured to be connected to said case electrode and a right ventricular ring electrode to pick up said far-field intra-ventricular electrogram signal.

4. The heart stimulation device according to claim 1, wherein said processing unit is further configured to modulate said predefined VP spike template from a predefined VP template, so that a width of said predefined VP spike template is proportional to a measured VP pulse width, and wherein a height of said predefined VP spike template is proportional to a measured VP amplitude and further scaled based on VP polarity.

5. The heart stimulation device according to claim 1, wherein addition of said predefined VP spike template to said composite far-field electrogram signal can be enabled or disabled by a programmable VP pulse ON/OFF switch.

6. The heart stimulation device according to claim 1, wherein said scale of said far-field intra-atrial or said far-field intra-ventricular electrogram signal is defined by a gain factor that is adjustable.

7. The heart stimulation device according to claim 1, wherein said filter of said far-field intra-atrial or said far-field intra-ventricular electrogram signal is performed with a filler having adjustable filter characteristics.

8. The heart stimulation device according to claim 7, wherein said filter having adjustable filter characteristics comprises one or a cascade of filters with predefined filter characteristics, including filter type, corner frequency and phase delay.

9. The heart stimulation device of claim 1 coupled with an external device comprising an external telemetry unit that is configured to receive a data signal that represents said far-field intra-atrial electrogram signal and said far-field intra-ventricular electrogram signal; and, wherein said processing unit is indirectly connected to said atrial far-field sensing stage and said ventricular far-field sensing stage via said telemetry unit and said external telemetry unit.

10. A heart stimulation device comprising:

an atria far-field sensing stage that is connectable or connected to a electrode lead having at least one atrial sensing electrode for intra-atrial placement, wherein said atrial far-field sensing stage is configured to process electric signals picked up via said at least one atrial sensing electrode and to generate therefrom a far-field infra-atrial electrogram signal;

a ventricular far-field sensing stage that is connectable or connected to a second electrode lead having at least one ventricular sensing electrode for intra-intraventricular placement, wherein said ventricular far-field sensing stage is configured to process electric signals picked up via said at least one ventricular sensing electrode and to generate therefrom a far-field intra-ventricular electrogram signal;

a processing unit that is coupled with said atrial far-field sensing stage and said ventricular far-field sensing stage and that is configured to independently filter, scale, and then sum, said filtered and scaled far-field intra-atrial electrogram and said filtered and scaled far-field intra-ventricular electrogram to form a composite far-field electrogram signal; and, a telemetry unit that is at least indirectly connected to said processing unit and that is configured to transmit data signal that represents said composite far-field electrogram signal;

wherein said heart stimulation device comprises at least one stimulation pulse generator that is connectable or connected to an intra-atrial stimulation electrode and that is configured to generate an atrial stimulation pulse that is delivered via said intra-atrial stimulation electrode;

wherein said heart stimulation device comprises a control unit that is configured to control said atrial far-field sensing stage and/or said ventricular far-field sensing stage to be blanked, when an atrial stimulation pulse is delivered, and generate an Atrial Pace or AP marker signal when an atrial stimulation pulse is delivered; and, wherein said processing unit is configured to add a predefined AP spike template to said composite signal when said AP marker signal is received.

11. The heart stimulation device according to claim 10, wherein said processing unit is further configured to modulate said predefined AP spike template from a predefined AP template, so that a width of said predefined AP spike template is proportional to a measured AP pulse width, and wherein a height of said predefined AP spike template is proportional to a measured AP amplitude and further scaled based on AP polarity.

12. The heart stimulation device according to claim 10, wherein addition of said predefined AP spike template to said composite far-field electrogram signal can be enabled or disabled by a programmable AP pulse ON/OFF switch.

13. The heart stimulation device according to claim 10, wherein said heart stimulation device is an implantable cardioverter/defibrillator configured to be connected to a shock lead providing a superior vena cava or SVC shock coil and a right ventricular shock coil and wherein said heart stimulation device further comprises a case providing an electrically conducting surface that forms a case electrode and wherein said atrial far-field sensing stage is configured to be connected to said case electrode and said superior vena cava shock coil to pick up said far-field intra-atrial electrogram signal and wherein said ventricular far-field sensing stage is configured to be connected to said case electrode and said right ventricular shock coil to pick up said far-field intra-ventricular electrogram signal.

14. The heart stimulation device according to claim 10, wherein said heart stimulation device comprises a case that provides an electrically conducting surface that forms a case electrode and wherein said atrial far-field sensing stage is configured to be connected to said case electrode and an atrial ring electrode to pick up said far-field intra-atrial electrogram signal and wherein said ventricular far-field sensing stage is configured to be connected to said case electrode and a right ventricular ring electrode to pick up said far-field intra-ventricular electrogram signal.

15. The heart stimulation device according to claim 10, wherein said scale of said far-field intra-atrial or said far-field intra-ventricular electrogram signal is defined by a gain factor that is adjustable.

16. The heart stimulation device according to claim 10, wherein said filter of said far-field intra-atrial or said far-field intra-ventricular electrogram signal is performed with a filter having adjustable filter characteristics.

17. The heart stimulation device according to claim 16, wherein said filter having adjustable filter characteristics comprises one or a cascade of filters with predefined filter characteristics, including filter type, corner frequency and phase delay.

18. The heart stimulation device of claim 10 coupled with an external device comprising
an external telemetry unit that is configured to receive a data signal that represents said far-field intra-atrial electrogram signal and said far-field intra-ventricular electrogram signal; and,
wherein said processing unit is indirectly connected to said atrial far-field sensing stage and said ventricular far-field sensing stage via said telemetry unit and said external telemetry unit.

19. A heart stimulation device comprising:
an atrial far-field sensing stage that is connectable or connected to a first electrode lead having at least one atrial sensing electrode for infra-atrial placement, wherein, said atrial far-field sensing stage is configured to process electric signals picked up via said at least one atrial sensing electrode and to generate therefrom a farf-field intra-atrial electrogram signal;
a ventricular far-field sensing stage that is connectable or connected to a second electrode lead having at least one ventricular sensing electrode for intra-ventricular placement, wherein said ventricular sensing far-field sensing stage is configured to process signals picked up via said at least one ventricular sensing electrode and to generate therefrom a far-field intra-ventricular electrogram signal;
a processing unit is coupled said atrial far-field sensing stage and said ventricular far-field sensing stage and that is configured to independently filter, scale, and then sum said filtered and scaled far-field intra-atrial electrogram and said filtered and scaled far-field intra-ventricular electrogram to form a composite far-field electrogram signal; and,
a telemetry unit that is at least indirectly connected to said processing unit and that is configured to transmit a data signal that represents said composite far-field electrogram signal;
wherein said processing unit comprises at least one second level filter configured to fitter said composite far-field electrogram signal;
wherein said processing unit comprises a plurality of second level filters including optimized filters for Atrial Sense or AS, Ventricular Sense or VS, Atrial Pace or AP, and Ventricular Pace or VP events, wherein said processing unit is configured to filter with said plurality of second level filters with respect to time window that immediately follows respective event types AS, VS, AP or VP, and wherein said processing unit is further configured to filter with a generic filter with respect to an Intracardiac Electrogram or IEGM segment after said window.

20. A heart stimulation device comprising:
an atria far-field sensing stage that is connectable or connected to a first electrode lead having at least one atrial sensing electrode for intra-atrial placement, wherein said atrial far-field sensing stage is configured to process electric signals picked up via said at least one atrial sensing electrode and to generate therefrom a far-field intra-atrial electrogram signal;
a ventricular far-field sensing stage that is connectable or connected to a second electrode lead having at least one ventricular sensing electrode for intra-ventricular placement wherein said ventricular far-field sensing stage is configured to process electric signals picked up via said at least one ventricular sensing electrode and to generate therefrom a far-field intra-ventricular electrogram signal;
a processing unit that is coupled with said atrial far-field sensing stage and said ventricular far-field sensing stage and that is configured to independently filter, scale, and then sum said filtered and scaled far-field intra-atrial electrogram and said filtered and scaled far-field, intra-ventricular electrogram to form a composite far-field electrogram signal; and,
a telemetry unit that is at least indirectly connected to said processing unit and that is configured to transmit a data signal that represents said composite far-field electrogram signal;
wherein said processing unit comprises a ventricular far-field electrogram amplifier and is configured to calculate a ratio of a desired R wave amplitude to a measured peak amplitude of a ventricular depolarization complex, and to adjust a ventricular gain factor to be applied by said ventricular far-field electrogram amplifier to said far-field intra-ventricular electrogram signal.

21. The heart stimulation device according to claim 20, wherein said processing unit is configured to measure peak amplitudes of said ventricular depolarization complex and/or to measure an average of absolute peak amplitudes of a predetermined number of latest multiple Ventricular Sense or VS complexes.

22. The heart stimulation device according to claim 21, wherein said processing unit is further configured to perform said measurement upon receipt of a user command during device implant or follow-up.

23. A heart stimulation device comprising:

an atrial far-field sensing stage that is connectable or connected to a first electrode lead having at least one atrial sensing electrode for intra-atrial placement, wherein said atrial far-field sensing stage is configured to process electric signals picked up via said at least one atrial sensing electrode and to generate therefrom a far-field intra-atrial electrogram, signal;

a ventricular far-field sensing stage that is connectable or connected to a second electrode lead having at least one ventricular sensing electrode for intra-ventricular placement wherein said ventricular far-field sensing stage is configured to process electric signals picked up via said at least one ventricular sensing electrode and to generate therefrom a far-field intra-ventricular electrogram signal;

a processing unit that is coupled with said atrial far-field sensing stage and said ventricular far-field sensing stage and that is configured to independently filter, scale, and then sum, said filtered and scaled far-field intra-atrial electrogram and said filtered and scaled thr field intra-ventricular electrogram to form a composite far-field electrogram signal; and, a telemetry unit that is at least indirectly connected to said processing unit and that is configured to transmit a data signal that represents said composite far electrogram signal;

wherein said processing unit comprises an atrial far-field electrogram amplifier and is configured to calculate a ratio of a desired P wave amplitude to a measured peak amplitude of an atrial depolarization complex, and to adjust an atrial gain factor to be applied by said atrial far-field electrogram amplifier to said far-field intra-atrial electrogram signal.

24. The heart stimulation device according to claim 23, wherein said processing unit is configured to measure peak amplitudes of said atrial depolarization complex and/or to measure an average of absolute peak amplitude of a predetermined number of latest multiple Atrial Sense or AS complexes.

\* \* \* \* \*